US00PP19898P2

(12) United States Plant Patent
Chez

(10) Patent No.: US PP19,898 P2
(45) Date of Patent: Apr. 7, 2009

(54) ***HAKONECHLOA* PLANT NAMED 'NICOLAS'**

(50) Latin Name: *Hakonechloa macra*
Varietal Denomination: Nicolas

(76) Inventor: Olivier Bennato Chez, 203 Avenue De Pépinières Fleurs 515, Min Rungis Cedex (FR), 94648

( * ) Notice: Subject to any disclaimer, the term of this patent is extended or adjusted under 35 U.S.C. 154(b) by 0 days.

(21) Appl. No.: 12/080,053

(22) Filed: Mar. 31, 2008

(51) Int. Cl.
*A01H 5/00* (2006.01)

(52) U.S. Cl. ..... Plt./384

(58) Field of Classification Search ..... Plt./384
See application file for complete search history.

*Primary Examiner*—Annette H Para
(74) *Attorney, Agent, or Firm*—Penny J. Aguirre

(57) ABSTRACT

A new and unique cultivar of *Hakonechloa* named 'Nicolas' that is characterized by its green to yellow green foliage in the spring and summer that turns deep red fall. As the mature foliage changes to a red with cool temperatures, a combination of summer and fall foliage creates a unique combination of foliage color. 'Nicolas' is further characterized by its dwarf plant habit, its hardiness in U.S.D.A. Zones 5 to 9, and its relatively vigorous growth habit.

2 Drawing Sheets

RELATED APPLICATIONS

This application is co-pending with U.S. Plant Patent application number 12/079,983 filed for a cultivar selected by the same inventor entitled *Hakonechloa* Plant Named 'Naomi'.

Botanical classification: *Hakonechloa macra.*

Varietal designation: 'Nicolas'.

BACKGROUND OF THE INVENTION

The present invention relates to a new and distinct cultivar of *Hakonechloa macra* and will be referred to hereafter by its cultivar name, 'Nicolas'. 'Nicolas' represents a new cultivar of Hakone grass, an ornamental grass grown for landscape use.

The inventor discovered the new cultivar, 'Nicolas', in a cultivated trial garden in Min Rungis Cedex, France as a naturally occurring whole plant mutation in fall of 2003. The inventor had been growing and selecting unnamed seedlings of *Hakonechloa macra* in his trail garden for many years and therefore, the parent plants of 'Nicolas' are unknown.

Asexual reproduction of the new cultivar was first accomplished by stem division in Min Rungis Cedex, France in spring 2004 by the inventor. The characteristics of this cultivar have been determined to be stable and are reproduced true to type in successive generations.

SUMMARY OF THE INVENTION

The following traits have been repeatedly observed and represent the characteristics of the new cultivar as grown outdoors in a trial garden for five years in Min Rungis Cedex, France. These attributes in combination distinguish 'Nicolas' as a unique cultivar of *Hakonechloa.*

1. 'Nicolas' exhibits non-variegated foliage that is green to yellow green in the spring and summer and turns deep red in fall. As the mature foliage turns red with cool temperatures, the combination of summer and fall foliage creates a unique combination of foliage color.

2. 'Nicolas' exhibits a dwarf plant habit reaching about 24 cm in height in bloom with the foliage reaching about 15 cm in height.
3. 'Nicolas' is suitable for use as an edging and groundcover plant.
4. 'Nicolas' is hardy in U.S.D.A. Zones 5 to 9.
5. 'Nicolas' blooms in summer with airy panicles above the foliage.

'Nicolas' can be most closely compared to *Hakonechloa macra* 'Beni-Kaze' (unpatented) and 'Naomi', another cultivar selected by the inventor. 'Beni-Kaze' is similar in having non-variegated foliage with intense red fall color, however the foliage of 'Beni-Kaze' is more green than yellow-green and 'Beni-Kaze' is a taller plant. 'Naomi' is similar to 'Nicolas' in height and also attains an intense red fall color, however the summer foliage of 'Naomi' is variegated and the fall color is more purple in color.

BRIEF DESCRIPTION OF THE DRAWING

The accompanying colored photographs illustrate the overall appearance and distinct characteristics of the new *Hakonechloa.*

The photograph on the first sheet was taken in September of a 3 year old plant of 'Nicolas' a grown in a trial garden in The Netherlands and illustrates the fall coloration of 'Nicolas'.

The photographs on the second sheet were taken in late summer of 3 year-old plants of 'Nicolas' as grown in a 26 cm container in The Netherlands.

The photograph on the top of the second sheet is a close-up view of the foliage with a combination of yellow green summer foliage and red fall foliage.

The photograph on the bottom of the second sheet provides a close-up view of the flower panicles.

The colors in the photographs are as close as possible with the digital photography techniques available, the color values cited in the detailed botanical description accurately describe the colors of the new *Hakonechloa.*

BOTANICAL DESCRIPTION OF THE PLANT

The following is a detailed description of 3 year-old plants of 'Nicolas' as grown outdoors in 26 cm containers in The Netherlands. The plants were grown in average day temperatures of 13° to 27° C. and average night temperatures of 4° to 14° C. under ambient light. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

General description:

*Blooming habit.*—Blooms in mid summer.

*Plant habit.*—Herbaceous, clump-forming, slowly spreading ornamental grass forming a mound of bamboo-like cascading foliage, suitable for use as a groundcover or edging plant.

*Height and spread.*—Exhibits a dwarf plant habit reaching about 24 cm in height in bloom with the foliage reaching 15 cm in height with a spread of about 61 cm.

*Hardiness.*—U.S.D.A. Zones 5 to 9.

*Culture.*—Performs best in moist, well drained, organic rich soils in partial or part shade.

*Diseases and pests.*—No susceptibility or resistance to diseases or pests has been observed.

*Root description.*—Fibrous.

Growth and propagation:

*Propagation.*—Tissue culture and stem division.

*Vigor.*—More vigorous than is typical of *Hakonechloa macra* selections.

Culm (stem) description:

*General.*—Round, sheathed.

*Culm color.*—146A to 146B and tinged with 183A to 183B near nodes.

*Culm size.*—Average of 13 cm in length and 1 m in length.

*Stem surface.*—Glabrous, slightly glossy.

*Stem number.*—About 130 (3 year-old plant).

*Internode length.*—Average of 2.6 cm.

*Branching.*—Basal branches only, no lateral branches.

Foliage description:

*Leaf shape.*—Linear.

*Leaf division.*—Simple.

*Leaf base.*—Cuneate and decurrent at stem.

*Leaf apex.*—Acuminate.

*Leaf aspect.*—Held from horizontal to cascading downward.

*Leaf venation.*—Parallel, matching leaf color.

*Leaf margins.*—Entire, with sharp short bristles that are not visually noticeable.

*Leaf attachment.*—Sheathed.

*Leaf size.*—Average of 8 mm in width and 11.9 cm in length.

*Leaf number.*—Average of 5 per culm.

*Leaf arrangement.*—Alternate.

*Ligule.*—A band of tufted hairs, 0.6 mm in length and N155A in color.

*Leaf surface.*—Glabrous and slightly glossy on upper and lower surface with bristles on margins.

*Leaf color.*—Young leaves, upper surface; 145A and 150B towards base, young leaves, lower surface; N144A and 150B towards base, mature leaves, upper surface; 176A to 178A and 177B towards base, mature leaves, lower surface; color between 177C to 177D and 199C to 199D and 146C to 146D towards base. The color ranges stated are dependent on temperature and light levels.

Inflorescence description:

*General description.*—Terminal airy panicle of single spikelets.

*Lastingness of inflorescence.*—Each panicle blooms for about 3 weeks, persistent.

*Fragrance.*—None.

*Panicle size.*—Average of 7.8 cm in length and up to 4.3 cm in width.

*Panicle number.*—One per culm.

*Rachis size.*—Up to about 6.4 cm in length, continuous with culm, 0.8 mm in diameter, with rachilla emerging at about a 45° angle to main branch about 7 cm in length and less than 0.8 mm in diameter, N143B in color.

*Spikelet bud.*—About 6 mm in length and 1 mm in width, narrow lanceolate in shape, 145C to 145D in color.

*Spikelet description.*—Single floret enclosed by one glume and one lemma, glume; lanceolate in shape with a glabrous surface, entire margin, acute apex, 4 mm in length, 0.5 mm in width and 145D in color with the tip 181 B to 181 C, lemma; lanceolate in shape with a glabrous surface, entire margin, acute apex, 6.5 mm in length, 1 mm in width and 145D in color with the tip 181 B to 181 C.

*Spikelet number.*—Average of 100 per panicle.

*Spikelet size.*—About 6.5 mm in length and 4 mm in width.

Reproductive organs:

*Stamens.*—2, anthers are dorsifixed, x-shaped, about 2 mm in length and 187A in color, pollen is very low in quantity and 162A to 162B in color.

*Pistils.*—2, about 1.5 mm in length, stigma is fimbriate in shape, about 0.5 mm in length, and N77C in color, style; transparent in color, about 0.5 mm in length, ovary is 145A in color.

*Seed.*—No seed development has been observed.

It is claimed:

1. A new and distinct cultivar of *Hakonechloa* plant named 'Nicolas' as herein illustrated and described.

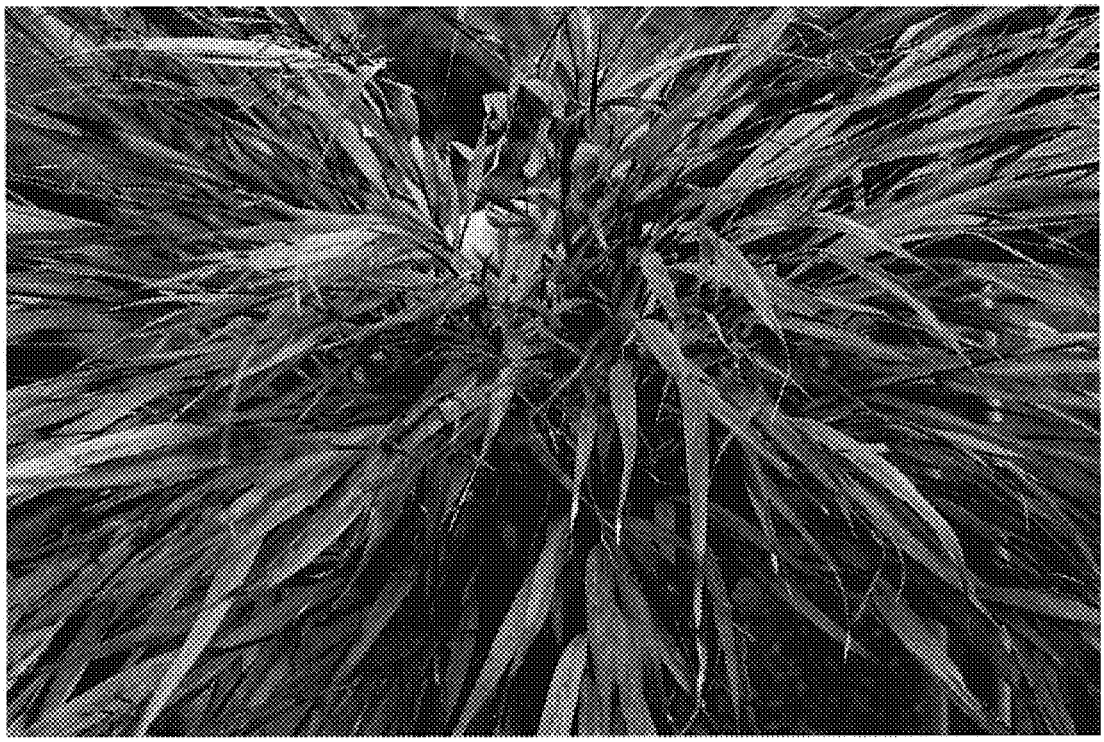

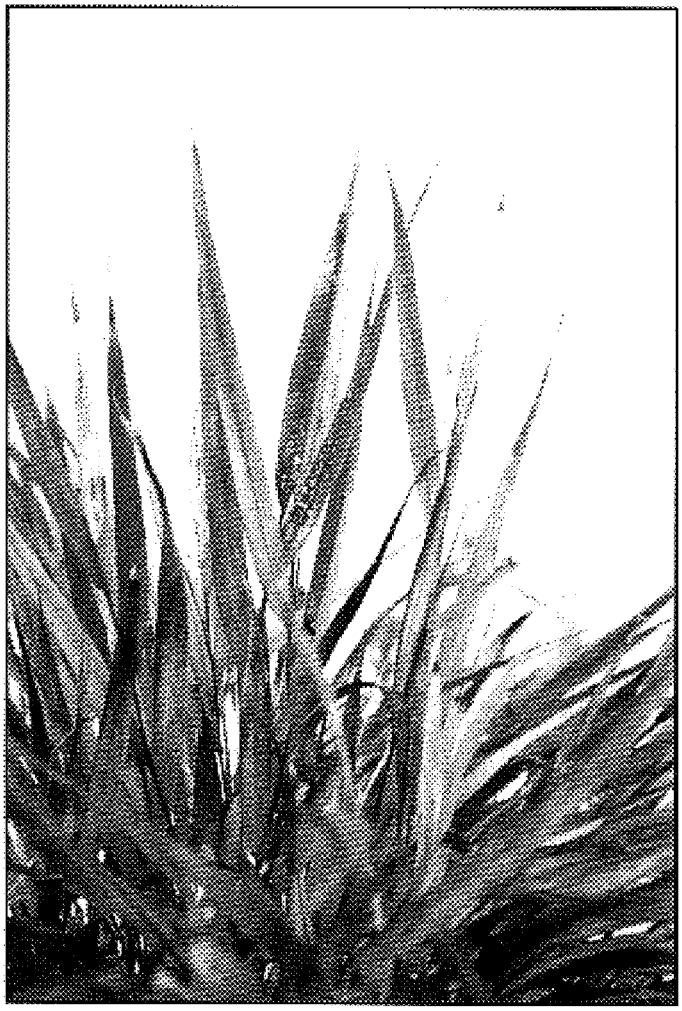
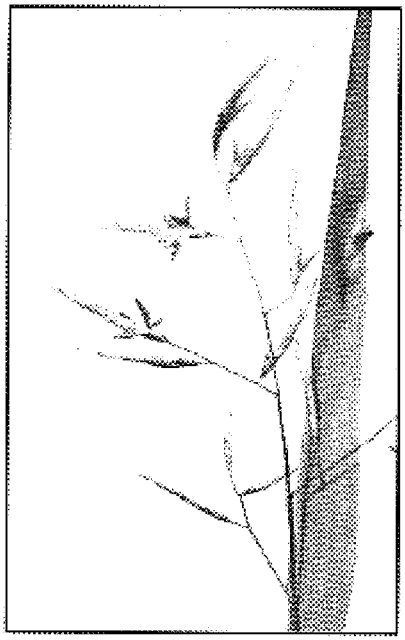

* * * * *